(12) United States Patent
Lim et al.

(10) Patent No.: US 9,822,149 B2
(45) Date of Patent: Nov. 21, 2017

(54) POLYPEPTIDE HAVING MULTIPLE DIRECTIONALITY AND SELF-ASSEMBLED NANOSTRUCTURE CONTAINING THE SAME

(71) Applicant: INDUSTRY-ACADEMIC COOPERATION FOUNDATION, YONSEI UNIVERSITY, Seoul (KR)

(72) Inventors: Yong-Beom Lim, Seoul (KR); Woo-Jin Jeong, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 36 days.

(21) Appl. No.: 14/606,277

(22) Filed: Jan. 27, 2015

(65) Prior Publication Data

US 2015/0274783 A1 Oct. 1, 2015

(30) Foreign Application Priority Data

Mar. 26, 2014 (KR) ........................ 10-2014-0035195

(51) Int. Cl.
*A61K 38/00* (2006.01)
*C07K 14/00* (2006.01)
*C07K 7/08* (2006.01)

(52) U.S. Cl.
CPC .............. *C07K 14/001* (2013.01); *C07K 7/08* (2013.01); *Y10T 428/31768* (2015.04)

(58) Field of Classification Search
None
See application file for complete search history.

(56) References Cited

FOREIGN PATENT DOCUMENTS

KR 1020020079731 10/2002
KR WO 2010/074542 * 7/2010

OTHER PUBLICATIONS

Zhang, S., "Fabrication of novel biomaterials through molecular self-assembly," Nature Biotechnology, Oct. 2003, vol. 21, No. 10, pp. 1171-1178.
Klok, H.A., "Protein-Inspired Materials: Synthetic Concepts and Potential Applications," Angew. Chem. Int. Ed., 2002, vol. 41, No. 9, pp. 1509-1513.
Gazit, E., "Self-assembled peptide nanostructures: the design of molecular building blocks and their technological utilization," Chem. Soc. Rev., 2007, vol. 36, pp. 1263-1269.
Lim, Y.B., et al., "Recent advances in functional supramolecular nanostructures assembled from bioactive building blocks," Chem. Soc. Rev., 2009, vol. 38, pp. 925-934.
Fletcher, John., et al., "Self-Assembling Cages from Coiled-Coil Peptide Modules," Science, May 2013, vol. 340, pp. 595-599.
Kuroda, Y., et al., "Oligopeptide-Mediated Stabilization of the α-Helix of a Prion Protein Peptide," J. Am. Chem. Soc., 2000, vol. 122, pp. 12596-12597.
Han, S., et al., "Structural and Conformational Dynamics of Self-Assembling Bioactive β-Sheet Peptide Nanostructures Decorated with Multivalent RNA-Binding Peptides," J. Am., Chem. Soc., 2012, vol. 134, pp. 16047-16053.

* cited by examiner

*Primary Examiner* — Jeanette Lieb
(74) *Attorney, Agent, or Firm* — Duane Morris LLP; J. Rodman Steele, Jr.; Gregory M. Lefkowitz

(57) ABSTRACT

The present disclosure relates to a polypeptide having multiple directionality and a self-assembled nanostructure containing the same. Since R1 and R3 domains having β-sheet structures are arranged to have antiparallel structures, it provides a more stabilized α-helix structure than the existing polypeptide having single directionality. In addition, since the polypeptide of the present disclosure is prepared as an antiparallel pseudo-cyclic structure without additional structural element such as a linker, the associated synthesis process is simple and the molecular weight is relatively small.
Since the polypeptide having multiple directionality having the structural and functional characteristics described above and a self-assembled nanostructure containing the same have excellent stability and transportability, they are applicable in various fields as drugs, for detection of substances in vivo, for targeting for drug delivery, and for inhibiting protein-mediated biomacromolecular interactions.

18 Claims, 14 Drawing Sheets

SEQUENCE LISTING

```
<160> NUMBER OF SEQ ID NOS: 13

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Trp Lys Trp Glu Trp Tyr Trp Lys Trp Glu Trp Gly Ser Gly Ser Glu
1               5                   10                  15

Ala Ala Ala Lys Glu Ala Ala Ala Lys Gly Ser Lys
            20                  25

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Lys Trp Glu Trp Tyr Trp Lys Trp Glu Trp
1               5                   10

<210> SEQ ID NO 3
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Glu Trp Lys Trp Tyr Trp Glu Trp Lys Trp
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Ala Ala Ala Lys
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Ala Ala Ala Glu
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ala Ala Lys
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 7

Gly Ser Gly Ser
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: See specification as filed for detailed
      description of substitutions and preferred embodiments

<400> SEQUENCE: 8

Gly Gly Gly Ser
1

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (9)..(10)
<223> OTHER INFORMATION: Residues at these positions are separated by an
      ebes moiety

<400> SEQUENCE: 9

Trp Lys Trp Glu Trp Gly Ser Gly Ser Gly Ser Lys
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Lys Trp Glu Trp
1               5

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (9)..(10)
<223> OTHER INFORMATION: Residues at these positions are separated by an
      ebes moiety

<400> SEQUENCE: 11

Gly Lys Gly Glu Gly Gly Ser Gly Ser Gly Ser Lys
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Trp Gly Glu Gly
1               5

<210> SEQ ID NO 13
<211> LENGTH: 30
<212> TYPE: PRT
<213> ORGANISM: Artificial Sequence

```
-continued

<220> FEATURE:
<223> OTHER INFORMATION: Description of Artificial Sequence: Synthetic
      polypeptide

<400> SEQUENCE: 13

Trp Lys Trp Glu Trp Tyr Trp Lys Trp Glu Trp Gly Ser Gly Ser Ala
1               5                   10                  15

Glu Ala Ala Ala Lys Glu Ala Ala Ala Lys Ala Gly Ser Lys
            20                  25                  30
```

POLYPEPTIDE HAVING MULTIPLE DIRECTIONALITY AND SELF-ASSEMBLED NANOSTRUCTURE CONTAINING THE SAME

CROSS-REFERENCE TO RELATED APPLICATIONS

This application claims priority under 35 U.S.C. §119 to Korean Patent Application No. 10-2014-0035195 filed on Mar. 26, 2014 in the Korean Intellectual Property Office, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 26, 2015, is named G1035-04801_SL.txt and is 3,934 bytes in size.

TECHNICAL FIELD

The present disclosure relates to a polypeptide having multiple directionality and a self-assembled nanostructure containing the same.

BACKGROUND

Biopolymers such as proteins or peptides assume three-dimensional structures suitable for their characteristic physiological functions through folding. Proteins are one of the naturally occurring substances that can perform the most various functions (non-patent documents 1-5).

Since the three-dimensional structure of proteins or peptides has to be conserved to maintain their activities in vivo, they are relatively expensive. In addition, they are very difficult to synthesize chemically because they are macromolecules with molecular weights of tens of KDa. Indeed, since natural peptides are easily degraded by various enzymes in the human body and have poor bioavailability, they are difficult to be used as injections or oral drugs and fail to maintain their activities in vivo.

To overcome this problem, methods of substituting the natural amino acids of the natural peptides with D-amino acids, modifying the terminal groups of the peptides, cyclizing the peptides, or the like, have been developed.

For instance, the prion protein (PrP) associated with amyloidosis contains an inhibitory peptide which can inhibit the change in three-dimensional structure. The inhibitory peptide chemically modifies the β-sheet breaker peptide, thereby providing good stability against proteases. A method of converting the inhibitory peptide to two or more inactive fragments has been developed (patent document 1).

Meanwhile, since a polypeptide having multiple directionality which acts on a three-dimensional protein structure having a βαβ motif can form a reproducible three-dimensional peptide structure, it is highly likely to be applied for biochips for diagnosis of diseases, electronic and other new materials including nanotubes, nanostructures necessary for the production of highly integrated semiconductors, and so forth.

However, the development of three-dimensional peptide structures has not been studied actively yet and a new type of peptide that can maintain the structural stability of a substrate recognition site of the peptide has never been reported.

REFERENCES OF THE RELATED ART

Patent Documents (Patent document 1) Korean Patent Publication No. 2002-0079731.

Non-Patent Documents (Non-patent document 1) Zhang, S. G. *Nat. Biotechnol.* 2003, 21, 1171.
(Non-patent document 2) Klok, H. A. *Angew. Chem. Int. Ed.* 2002, 41, 1509.
(Non-patent document 3) Gazit, E. *Chem. Soc. Rev.* 2007, 36, 1263.
(Non-patent document 4) Lim, Y. B.; Moon, K. S.; Lee, M. *Chem. Soc. Rev.* 2009, 38, 925.
(Non-patent document 5) Fletcher, J. M.; Hamiman, R. L.; Bames, F. R.; Boyle, A. L.; Collins, A.; Mantell, J.; Sharp, T. H.; Antognozzi. M.; Booth, P. J.; Linden, N.; Miles, M. J.; Sessions, R. B.; Verkade, P.; Woolfson, D. N. *Science.* 2013, 340, 595.

SUMMARY

The present disclosure is directed to providing a polypeptide having multiple directionality having a novel structure which is nonexistent in nature and a self-assembled nanostructure containing the same.

In an aspect, the present disclosure provides a polypeptide having multiple directionality, including R1, R2 and R3 domains, wherein a residue that links the R2 and the R3 is lysine (K) and the amino acid sequences of the R1 and the R3 have antiparallel structures.

The polypeptide may have a folded structure wherein the R2 domain having an α-helix structure is located at a center and the R1 and R3 domains having β-sheet structures are linked at both ends of the R2 domain.

The polypeptide may be represented by [Chemical Formula 1]:

[Chemical Formula 1]

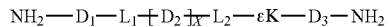

wherein
each of $D_1$, $D_2$ and $D_3$ consists of 1-20 amino acids,
each of $L_1$ and $L_2$ is a flexible linker consisting of 1-8 amino acids, and
X is an integer from 2 to 10.

The flexible linker may be selected from a group consisting of an amino acid consisting of glycine, an amino acid consisting of glycine and serine, an amino acid consisting of glycine and alanine and an amino acid consisting of alanine and serine.

The polypeptide having multiple directionality may have a sequence of [SEQ ID NOS 1 and 2]:

[SEQ ID NOs 1 and 2, respectively, in order of appearance]
WKWEWYWKWEW-GSGS-(EAAAK)$_2$-GS-eK-ẆĖẆḰẆẎẆĖẆḰẆ

(overhead dots for oppositely directed amino acid residues)

In another aspect, the present disclosure provides a self-assembled nanostructure formed as the polypeptide is self-assembled.

The self-assembled nanostructure may have a bilayer structure.

Since the polypeptide having multiple directionality of the present disclosure has a structure in which the R1 and R3 domains having β-sheet structures are arranged in multiple antiparallel directions, it provides a more stabilized α-helix structure as compared to a polypeptide having single directionality.

In addition, since the polypeptide of the present disclosure is prepared as an antiparallel pseudo-cyclic structure without additional structural element such as a linker, the associated synthesis process is simple and the molecular weight is relatively small.

Since the polypeptide having multiple directionality of the present disclosure having the structural and functional characteristics described above and a self-assembled nanostructure containing the same have excellent stability and transportability, they are applicable in various fields as drugs, for detection of substances in vivo and for targeting for drug delivery.

DETAILED DESCRIPTION OF EMBODIMENTS

Hereinafter, a polypeptide having multiple directionality and a self-assembled nanostructure according to the present disclosure will be described in more detail.

To provide a polypeptide having a stabilized α-helix structure, the inventors of the present disclosure have developed a polypeptide having multiple directionality, including R1, R2 and R3 domains, wherein a residue that links the R2 and the R3 is lysine (K) and the amino acid sequences of the R1 and the R3 have antiparallel structures.

The acronyms used in the present disclosure for amino acids and protecting groups are based on the terms recommended by the IUPAC-IUB Commission on Biochemical Nomenclature (*Biochemistry*, 11: 1726-1732 (1972)).

The term "polypeptide" used in the present disclosure refers to the total length of a polypeptide according to the present disclosure. In an exemplary embodiment, the "polypeptide" includes an isolated polypeptide, a polypeptide prepared by a recombination method, e.g., isolation from a sample followed by purification, and a polypeptide prepared by a common protein synthesis method, all of which are well known to those skilled in the art. Specifically, the entire polypeptide or a part thereof may be synthesized by a common synthesis method such as solid-phase peptide synthesis (Merrifield, R. B., *J. Am. Chem. Soc*, 85: 2149-2154 (1963)). In the present disclosure, an individual amino acid is often called an "amino acid residue" or an "amino acid".

Specifically, the primary structure of the polypeptide having multiple directionality according to the present disclosure is determined by the R1, R2 and R3 domains and the secondary structure is defined by the peptide backbone and the peptide segments such as α-helices, β-sheets and turns. For example, each of the R1, R2 and R3 domains forms a specific local secondary structure. Specifically, the R1 and R3 domains may have a 1-sheet structure and the R2 domain may have an α-helix structure. Accordingly, the three-dimensional shape of the polypeptide is directly related with the secondary structure.

In general, β-sheet strands have parallel or antiparallel structures through hydrogen bonding between them. The parallel structure is characterized by two β-sheet strands running in the same direction, from the N-terminal to the C-terminal, held together by hydrogen bonding between the strands. In contrast, the antiparallel structure is characterized by two β-sheet strands running in opposite directions held together by hydrogen bonding between the strands.

Figure 1:
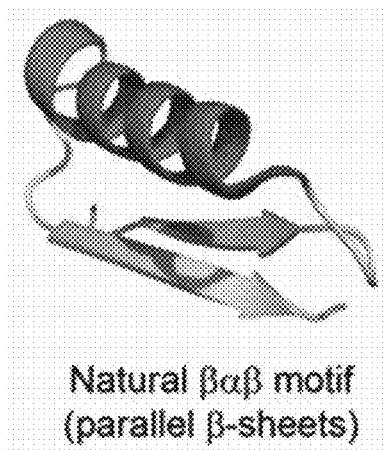
FIG. 1 schematically shows the structure of a polypeptide prepared in Comparative Example 2 (NDβ-Lα).
Figure 2:
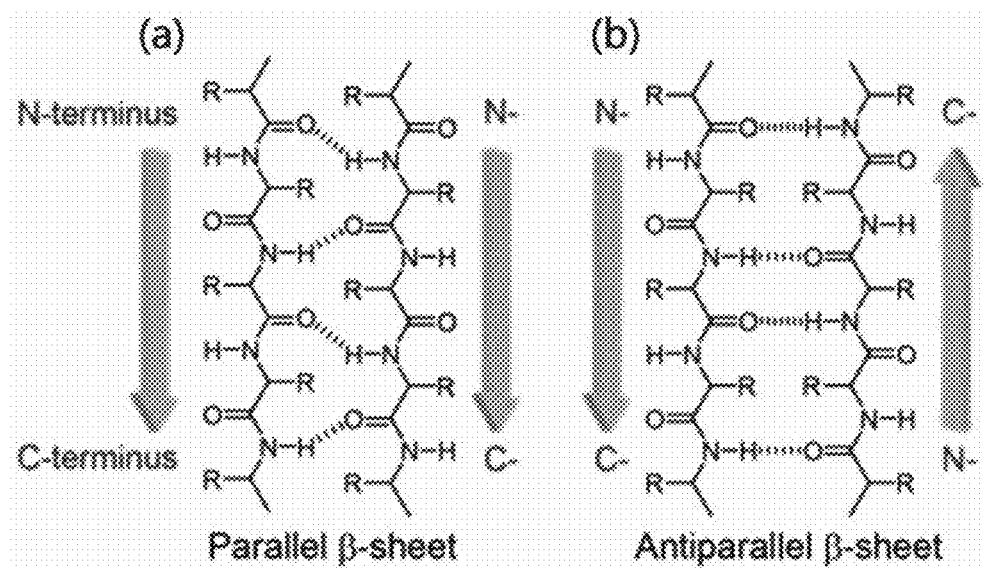
FIG. 2 shows the binding relationship of R1 and R3 domains of a polypeptide having multiple directionality according to the present disclosure. In a, the R1 and R3 domains are parallel to each other. In b, the R1 and R3 domains are antiparallel to each other.

The parallel or antiparallel structure may be differentiated from the number of atoms involved in the hydrogen bonding between the two strands. More specifically, the parallel structure involves 12 atoms and the antiparallel structure involves 10 or 14 atoms. The antiparallel structure is more stable than the parallel structure because the hydrogen bonding is linear with an angle of 180°. The parallel and antiparallel structures are described in FIG. 2.

In general, a natural polypeptide is synthesized in a direction from the N-terminal to the C-terminal. In particular, the existing β1-α-β2 motif polypeptide forms a parallel structure through hydrogen bonding between the β-sheets of β1 and β2. Since the antiparallel structure is more stable than the parallel structure, the adjacent β-sheets form the antiparallel structure. As a result, since the polypeptide aggregates with each other, it is unfolded without maintaining a stable α-helix structure (see FIG. 3).

In contrast, all the R1. R2 and R3 domains of the polypeptide having multiple directionality according to the present disclosure are synthesized in a direction from the C-terminal to the N-terminal, starting from lysine. The R1 and R3 domains have antiparallel structures through sequential deprotection reaction and controlled synthesis.

More specifically, the R3 domain is synthesized from the C-terminal toward the N-terminal through peptide bonding at the lysine residue. Accordingly, the polypeptide having multiple directionality according to the present disclosure has N-terminal amine groups at both terminals and is characterized by a new three-dimensional structure having double directionality (see FIG. 4).

The polypeptide having multiple directionality may be represented by [Chemical Formula 1]:

[Chemical Formula 1]

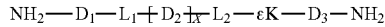

wherein
each of $D_1$, $D_2$ and $D_3$ comprises 1-20 amino acids,
each of $L_1$ and $L_2$ is a flexible linker comprising 1-8 amino acids, and
X is an integer from 2 to 10.

The $D_1$ and $D_3$ are not particularly limited as long as they have a β-sheet structure and consist of 1-20 amino acids. More specifically, they may be WKWEWYWKWEW (SEQ ID NO: or WEWKWYWEWKW (SEQ ID NO: 3).

The $D_2$ is not particularly limited as long as it has an α-helix structure and consists of 1-20 amino acids. More specifically, it may be EAAAK (SEQ ID NO: 4), KAAAE (SEQ ID NO: 5) or AAAK (SEQ ID NO: 6).

The $L_1$ and $L_2$ are not particularly limited as long as they are flexible linkers consisting of 1-8 amino acids known in the art. More specifically, they may be an amino acid consisting of glycine $((G)_n)$, an amino acid consisting of glycine and serine (e.g., $(GS)_n$, $(GSGS)_n$ (SEQ ID NO: 7) or $(GGGS)_n$ (SEQ ID NO: 8), wherein n is 1 or a larger integer), an amino acid consisting of glycine and alanine, an amino acid consisting of alanine and serine, or another flexible linker such as a tether for a Shaker potassium channel. But, an amino acid consisting of glycine is the most preferred because glycine can more effectively access the phi-psi space than alanine and is less restricted than other amino acid residues having long chains. In addition, since serine is hydrophilic and can dissolve the spherical glycine chain, a flexible linker consisting of glycine and serine is the most preferred.

The polypeptide having multiple directionality is a three-dimensional folded structure including a β1-α-β2 motif wherein the R2 domain having an α-helix structure is located at the center of the β1-α-β2 motif and the R1 and R3 domains including two strands of β-sheets are linked on both sides of the α-helix structure of R2. The R1 and R3 domains have antiparallel structures. The structure is illustrated in FIG. 4.

Figure 3:
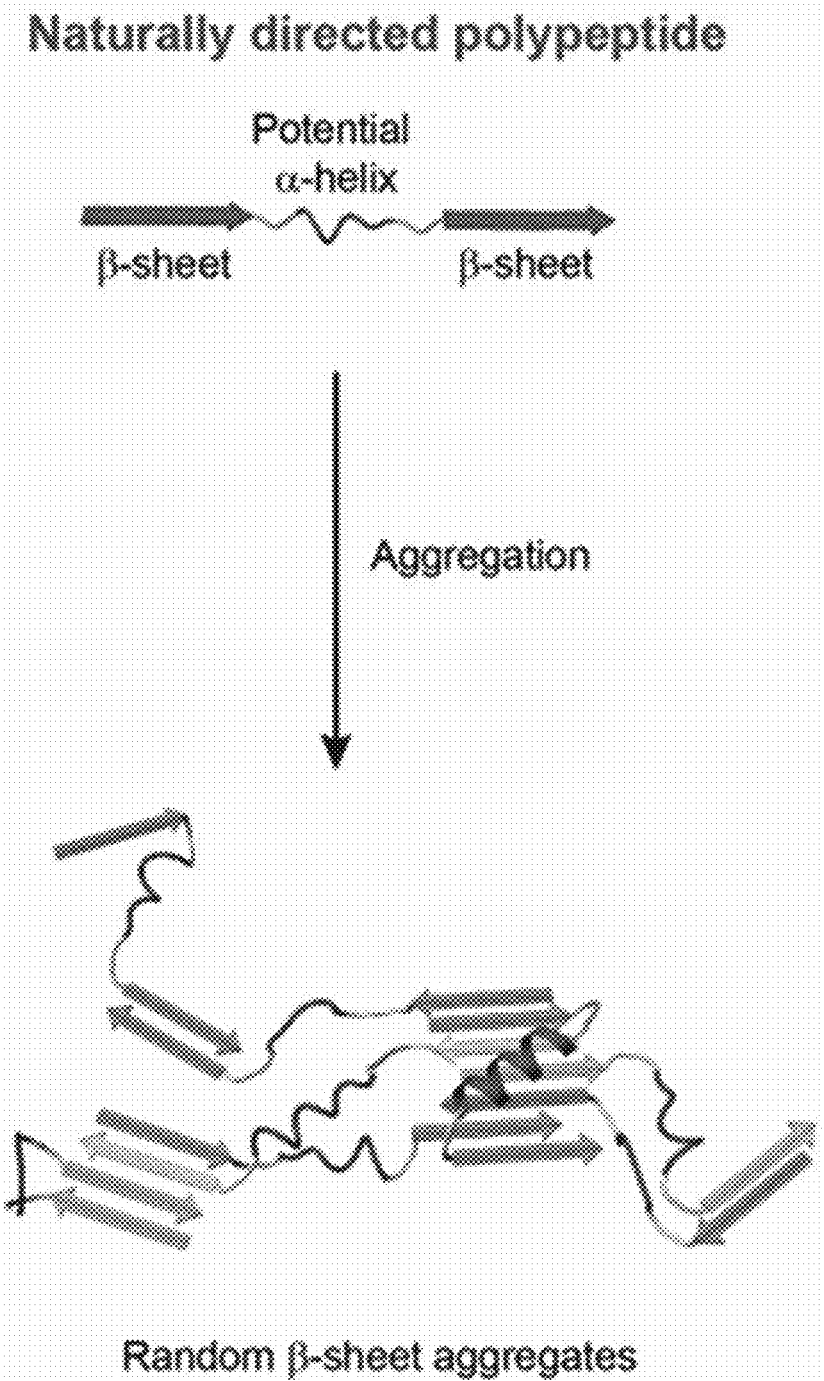
FIG. 3 schematically describes the structure and self-assembly of an existing naturally directed β1-α-β2 motif polypeptide.
Figure 4:
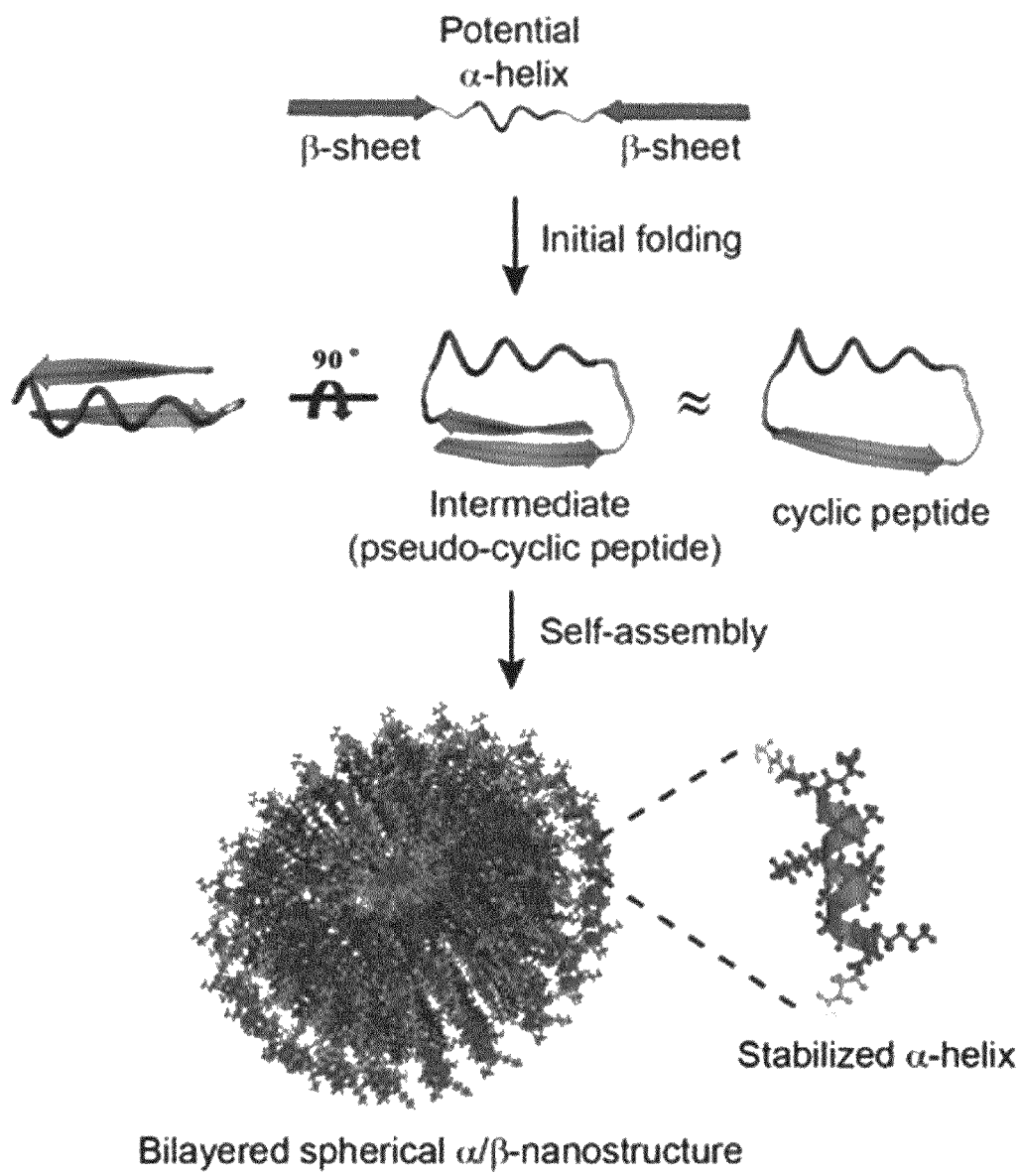
FIG. 4 schematically describes a polypeptide having multiple directionality according to the present disclosure and the structure of a self-assembled nanostructure containing the same.
Figure 5:
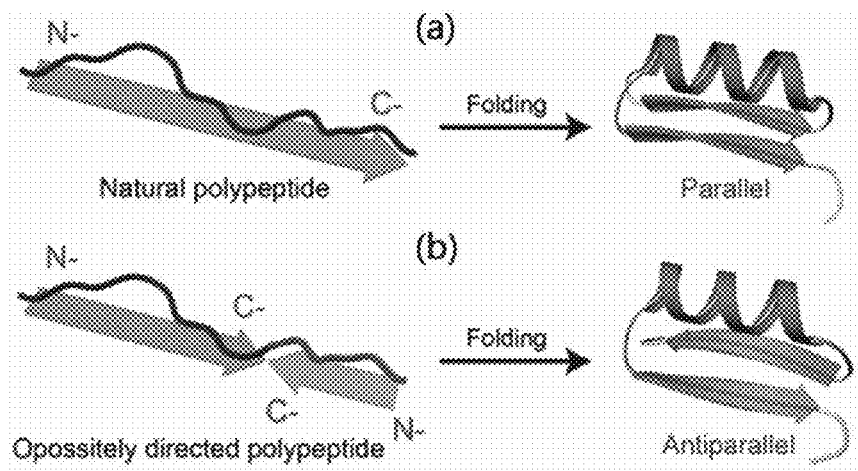
FIG. 5 schematically describes the folded structure of an existing β1-α-β2 motif polypeptide (a) and a polypeptide having multiple directionality according to the present disclosure (b).

FIG. 3 schematically describes the structure of an existing β1-α-β2 motif polypeptide and FIG. 4 schematically describes the structure of a polypeptide having multiple directionality according to the present disclosure and the structure of a self-assembled nanostructure containing the same.

As seen from FIG. 3, the existing β1-α-β2 motif polypeptide consists of β-sheets β1 and β2 and an α-helix α and is synthesized in a direction from the C-terminal to the N-terminal. Thus, the β1 and β2 β-sheets have parallel structures.

Since the parallel structure is less stable than the antiparallel structure, the β1 and/or β2 β-sheet strand easily forms a mixed structure in which antiparallel and parallel structures are mixed with the β1 and/or β2 β-sheet strand of another adjacent polypeptide. As a result, the existing β1-α-β2 motif polypeptide exists as an aggregate since the hydrogen bonding between the β-sheet strands is randomly mixed.

The existing β1-α-β2 motif polypeptide forming an aggregate is disadvantageous in that the α-helix structure which plays a critical role in substrate recognition is not stably maintained in the aggregate.

In contrast, as seen from FIG. 4, the polypeptide according to the present disclosure is similar to the existing β1-α-β2 motif polypeptide in basic structure, but is structurally different from the existing β1-α-β2 motif polypeptide in that the R1 and R3 domains having β-sheet structures have antiparallel structures.

The R3 domain is synthesized from the C-terminal toward the N-terminal through peptide bonding at the lysine residue (εK) of the polypeptide according to the present disclosure. Accordingly, the R1 domain and the R3 domain can have antiparallel structures.

In addition, in the polypeptide according to the present disclosure, the R1 and R3 domains form a pseudo-cyclic structure through hydrogen bonding and π-π interaction between the antiparallel structures of the two β-sheet strands. This constrains the α-helix structure of the R2 domain which plays a critical role in substrate recognition, thereby stabilizing the structure.

Since the α-helix structure of R2 which plays a critical role in substrate recognition can be maintained stably without modification owing to the pseudo-cyclic structure, stability and resistance against proteases in vivo are improved and substrate selectivity is increased.

In an exemplary embodiment, the R1, R2 and R3 domains of the polypeptide having multiple directionality according to the present disclosure may be selected from the Rev peptide derived from human immunodeficiency virus type I (HIV-I). The Rev peptide is an arginine-rich peptide that binds deeply within the RNA major groove of the HIV-1 Rev response element (RRE). It is already known that the α-helix of the Rev peptide is associated with the specific binding to the RRE RNA and aggregation does not occur.

In particular, the bottom-up self-assembly of supramolecular assemblies is a cost-effective method for constructing multivalent structures having biological activities.

Examples: Synthesis of ODβ-Lα Polypeptide

A peptide was synthesized on an amide MBHA resin according to the solid-phase peptide synthesis protocol. Fmoc (9-fluorenylmethyloxycarbonyl) and Dde (N-(1-(4,4-dimethyl-2,6-dioxocyclohexylidene)ethyl)) were used as amino acid protecting groups. The synthesis procedure is described in [Scheme 1].

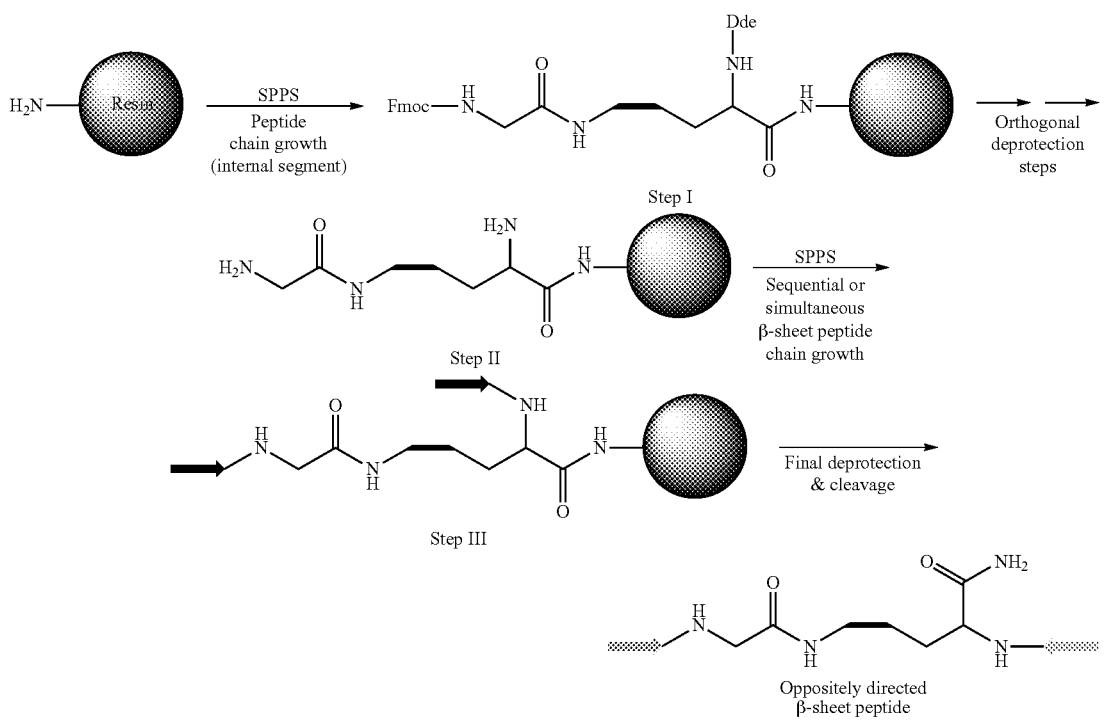

More specifically, the polypeptide having multiple directionality according to the present disclosure may be represented by [SEQ ID NOS 1 and 2].

```
                                    [SEQ ID NOs 1 and 2,
                      respectively, in order of appearance]
WKWEWYWKWEW-GSGS-(EAAAK)₂-GS-eK-WEWKWYWEWKW
```

(overhead dots for oppositely directed amino acid residues)

The polypeptide having multiple directionality according to the present disclosure stabilizes the α-helix through self-assembly and can be successfully formed into a self-assembled nanostructure containing a plurality of α-helices. The self-assembled nanostructure is shown in FIG. 4. The self-assembled nanostructure is designed as a bilayer structure having the α-helix structures on the surface and inside. An elaborately designed compound can be self-assembled as a nanostructure coated with a plurality of α-helices. The present disclosure is very useful since a plurality of α-helix structures can be stabilized using the polypeptide having multiple directionality without the process of chemical modification.

In order to remove the protecting groups from the both ends of the synthesized peptide, the Fmoc at the N-terminal was treated with 20% piperidine in N-methyl-2-pyrrolidone (NMP) and the Dde was treated with 2% hydrazine in dimethylformamide (DMF). Next, β1 and β2 β-sheet segments were sequentially synthesized at both ends of the peptide according to the solid-phase peptide synthesis protocol.

Finally, for cleavage and deprotection, the dried resin was treated with a cleavage mixture (TFA:1,2-ethanedithiol:thioanisole; 95:2.5:2.5) for 3 hours and the peptide obtained by precipitating with tert-butyl methyl ether (TBME) was purified by reverse-phase HPLC (using a water-acetonitrile mixture containing 0.1% TFA). The molecular weight was determined by MALDI-TOF mass spectrometry. HPLC analysis revealed that the purity of the peptide was 95% or higher. Also, the peptide concentration in 8 M urea was spectroscopically determined from the extinction coefficient of tryptophan at 280 nm (5,500 $M^{-1}$ $cm^{-1}$).

Figure 6:
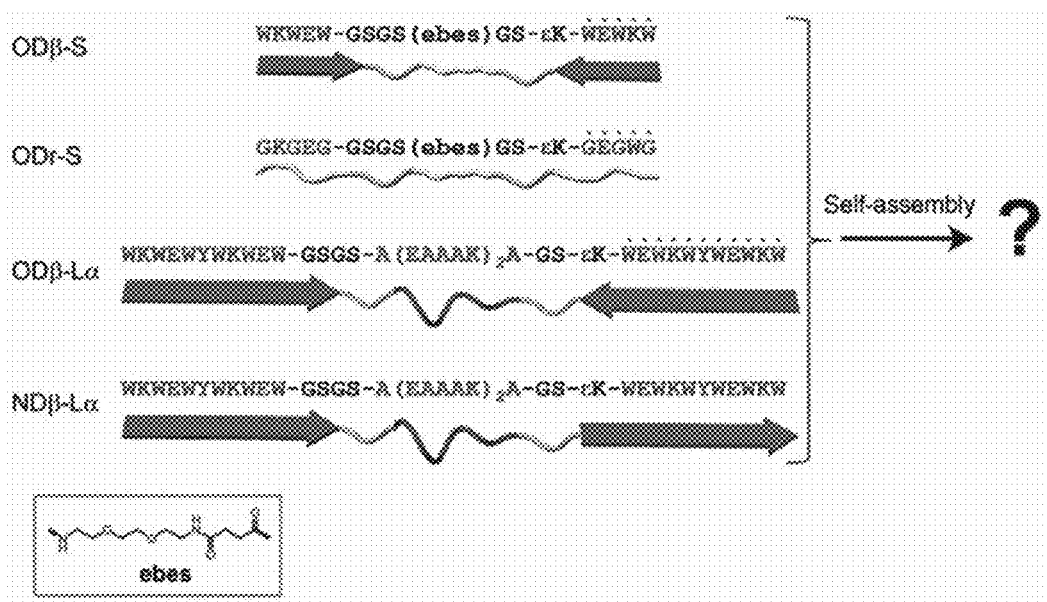
FIG. 6 schematically describes polypeptides prepared in Comparative Example 1 and Comparative Example 2 (ODr-S(SEQ ID NOS 11 and 12), NDβ-Lα (SEQ ID NOS 13 and 3)) and polypeptides prepared in Example 1 and Example 2 (ODβ-S (SEQ ID NOS 9 and 10), ODβ-Lα (SEQ ID NOS 13 and 2)).

The name and sequence of the prepared peptides are summarized in FIG. 6 and Table 1.

TABLE 1

| Peptide name | | Sequence |
|---|---|---|
| Example 1 | ODβ-Lα | WKWEWYWKWEW-GSGS-(EAAAK)$_2$-GS-eK-WEWKWYWEWKW (SEQ ID NOS 1 and 2) (overhead dots for oppositely directed amino acid residues) |
| Example 2 | ODβ-S | WKWEW-GSGS-(ebes)GS-εK-WEWKW (SEQ ID NOS 9 and 10) (overhead dots for oppositely directed amino acid residues) |
| Comparative Example 1 | ODr-S | GKGEG-GSGS-(ebes)GS-εK-GEGWG (SEQ ID NOS 11 and 12) (overhead dots for oppositely directed amino acid residues) |
| Comparative Example 2 | NDβ-Lα | WKWEWYWKWEW-GSGS-A(EAAAK)$_2$A-GS-εK-WEWKWYWEWKK (SEQ ID NOS 13 and 3) |

Figure 7:
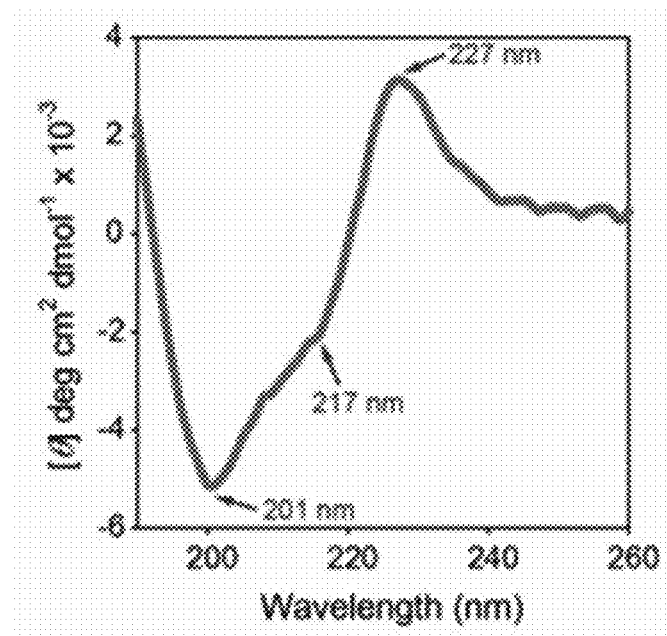
FIG. 7 shows a circular dichroism (CD) spectroscopy analysis result of a polypeptide prepared in Example 2 (ODβ-S).

FIG. 7 shows a circular dichroism (CD) spectroscopy analysis result of the polypeptide prepared in Example 2 (ODβ-S).

As seen from FIG. 7, negative bands were observed at 201 and 217 nm and a positive band was observed at 227 nm. This suggests that there is π-π interaction between the short β-sheets of β1 and β2 located at both ends of the polypeptide prepared in Example 2 (ODβ-S) and the tryptophan residue.

Figure 8:
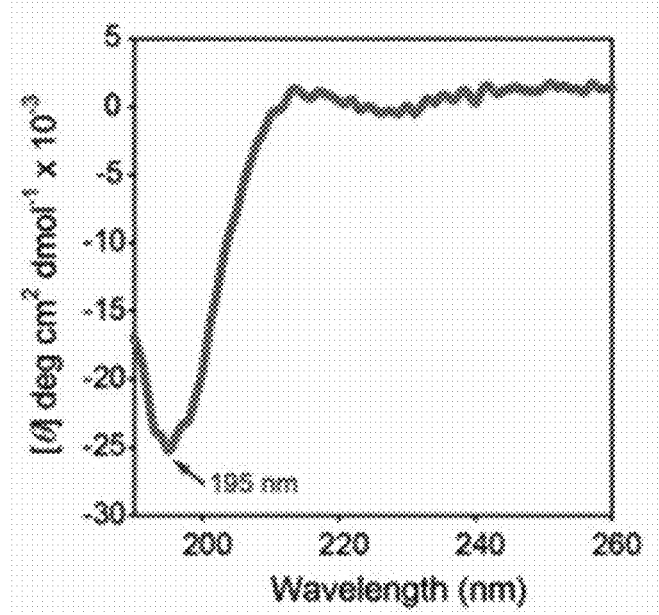
FIG. 8 shows a circular dichroism (CD) spectroscopy analysis result of a polypeptide prepared in Comparative Example 1 (ODr-S).

FIG. 8 shows a circular dichroism (CD) spectroscopy analysis result of the polypeptide prepared in Comparative Example 1 (ODr-S). The analysis was conducted at room temperature in distilled water.

As seen from FIG. 8, it can be seen that the polypeptide prepared in Comparative Example 1 (ODr-S) has a random structure because it does not include the β-sheet structure.

Figure 9:
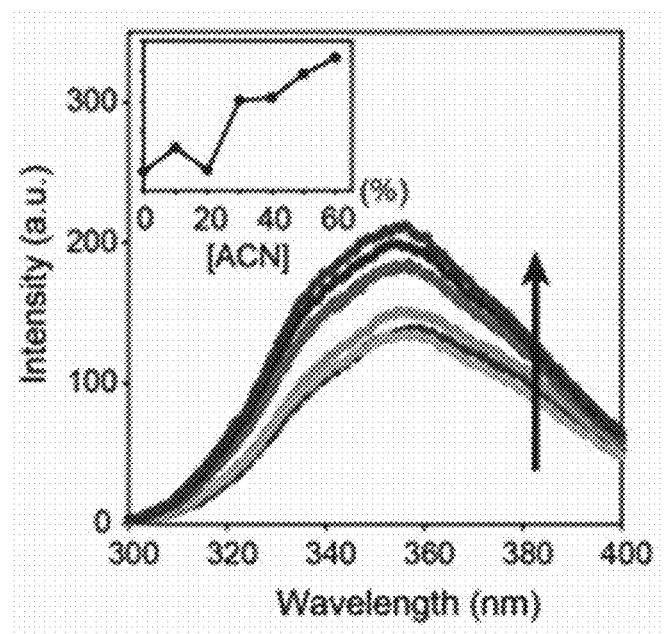
FIG. 9 shows a fluorescence analysis of a polypeptide prepared in Example 2 (ODβ-S) depending on the change in ACN concentration from 0 to 60%.

FIG. 9 shows a fluorescence analysis of the polypeptide prepared in Example 2 (ODβ-S) depending on the change in ACN concentration from 0 to 60%. The insert in FIG. 9 shows the fluorescence intensity at the maximum fluorescence wavelength of tryptophan (350 nm).

As seen from FIG. 9, it can be seen that the fluorescence intensity increases with the concentration of ACN (acetonitrile) and urea, probably because of fluorescence dequenching by CAN and urea.

Figure 10:
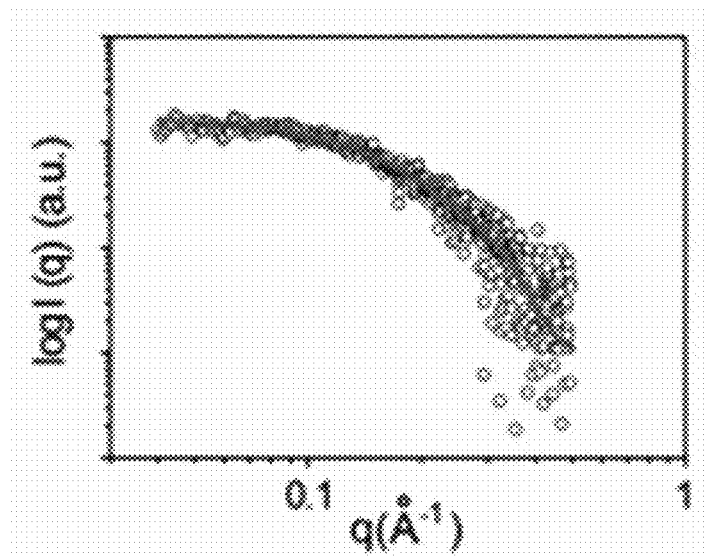
FIG. 10 shows small-angle X-ray scattering (SAXS) data of a polypeptide prepared in Example 2 (ODβ-S) in solution. The black circles represent experimental data and the red line represents X-ray scattering data of the most likely model obtained using DAMMIF.
Figure 11:
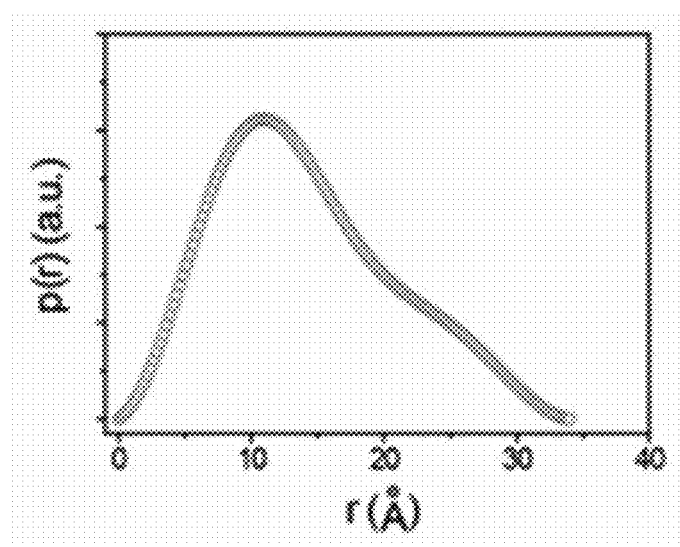
FIG. 11 shows an electron pair distance distribution function p(r) obtained from the experimental X-ray scattering data of FIG. 10 using GNOM.

FIG. 10 shows small-angle X-ray scattering (SAXS) data of the polypeptide prepared in Example 2 (ODβ-S) in solution. The black circles represent experimental data and the red line represents X-ray scattering data of the most likely model obtained using DAMMIF. FIG. 11 shows an electron pair distance distribution function p(r) obtained from the experimental X-ray scattering data of FIG. 10 using GNOM.

As shown in FIG. 10 and FIG. 11, a form factor (P(q)) and an electron pair distance distribution function p(r) were obtained to investigate the shape and size of the polypeptide prepared in Example 2 (ODβ-S).

For the polypeptide prepared in Example 2 (ODβ-S), $R_{g,p(r)}$ was calculated to be 11.01±0.078 Å and $D_{max}$ was calculated to be 34.0 Å. Through this, it can be seen that the polypeptide prepared in Example 2 (ODβ-S) exists as monomers rather than as aggregates.

Figure 12:
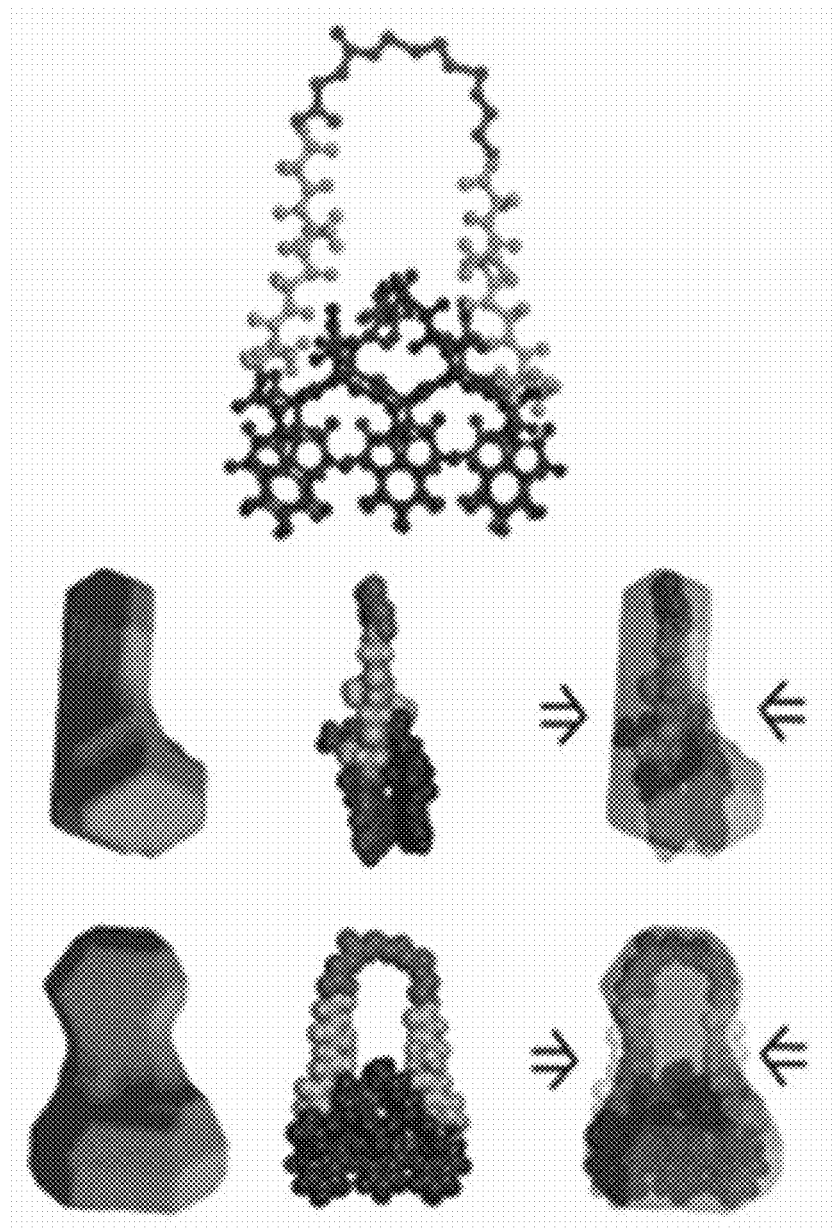
FIG. 12 shows the morphological structure of a polypeptide prepared in Example 2 (ODβ-S) obtained from the experimental X-ray scattering data of FIG. 10.

Also, from the insert in FIG. 9, it can be seen that the two β-sheet strands of β1 and β2 in the monomer molecules have antiparallel structures. This is consistent with FIG. 12 which shows the structure of the polypeptide prepared in Example 2 (ODβ-S).

Figure 13:
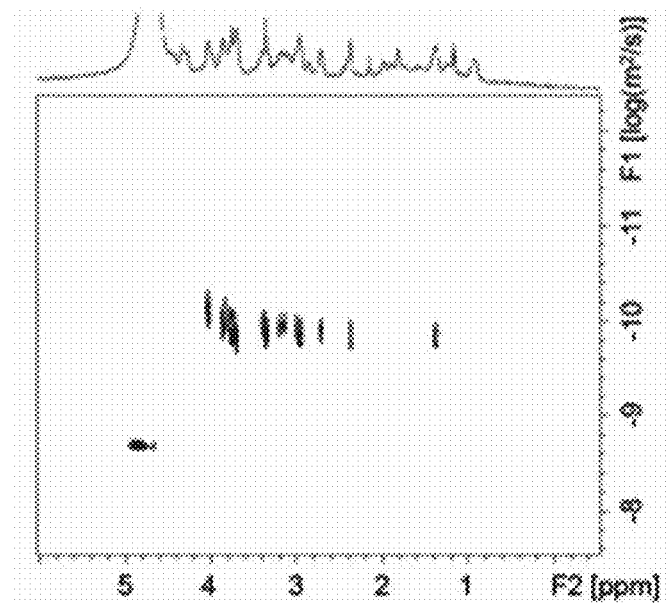
FIG. 13 shows a diffusion-ordered spectroscopy (DOSY) analysis result of a polypeptide prepared in Example 2 (ODβ-S) in solution.

FIG. 13 shows a diffusion-ordered spectroscopy (DOSY) analysis result of the polypeptide prepared in Example 2 (ODβ-S) in solution.

As seen from FIG. 13, the polypeptide prepared in Example 2 (ODβ-S) was found to have a hydrodynamic radius $R_{(H)}$ of 12.27 Å (D=1.625×10$^{-10}$ m$^2$/s). This result is consistent with the results of FIG. 11 and FIG. 12.

To conclude, it can be seen that the polypeptide prepared in Example 2 (ODβ-S) is a monomer including a β2 β-sheet in the molecule and forms a pseudo-cyclic structure.

Figure 14:
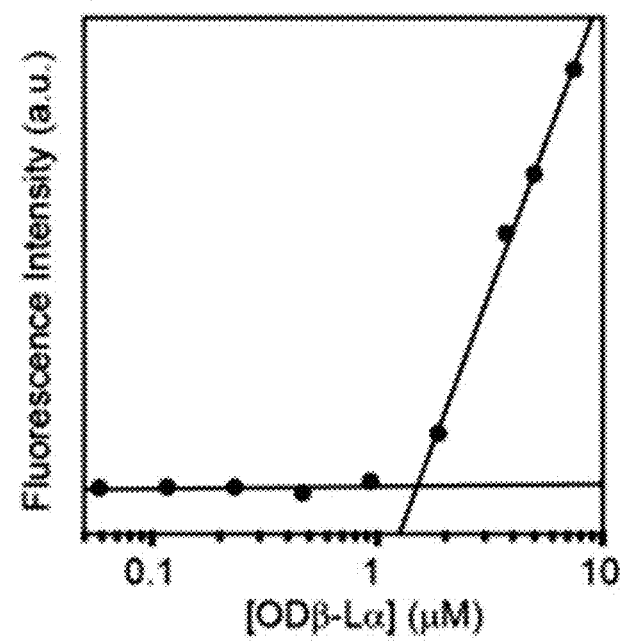
FIG. 14 shows a result of measuring the fluorescence intensity of a polypeptide prepared in Example 2 (ODβ-S) in solution for monitoring of the self-assembly process.
Figure 15:
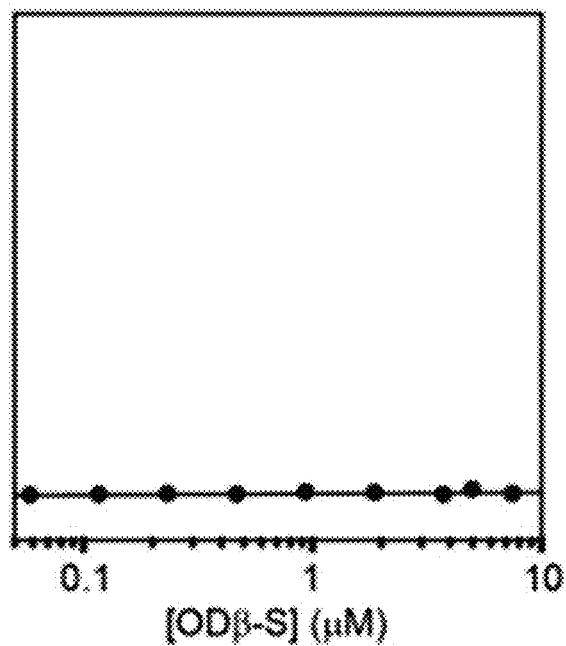
FIG. 15 shows a result of measuring the fluorescence intensity of a polypeptide prepared in Comparative Example 1 (ODr-S).

FIG. 14 shows a result of measuring the fluorescence intensity of the polypeptide prepared in Example 2 (ODβ-S) in solution for monitoring of the self-assembly process and FIG. 15 shows a result of measuring the fluorescence intensity of the polypeptide prepared in Comparative Example 1 (ODr-S). Thioflavin T (ThT) was used to probe the polypeptide prepared in Example 2 (ODβ-S). ThT is a fluorescent dye which displays enhanced fluorescence intensity when bound to the β-sheet of β1 and/or β2.

As seen from FIG. 14, the fluorescence intensity remained constant up to a certain concentration of the polypeptide prepared in Example 1 (ODβ-Lα) and then increased abruptly. For the polypeptide prepared in Example 2 (ODβ-S), the fluorescence intensity remained constant with concentration. This result suggests that the polypeptide prepared in Example 2 (ODβ-S) has a β-sheet of β1 and/or β2.

From the point of intersection of the extrapolated linear regression lines at discontinuity shown in FIG. 14, the critical aggregation concentration (CAC) of the polypeptide prepared in Example 1 (ODβ-Lα) was found to be 1.5 μM.

Meanwhile, the polypeptide prepared in Comparative Example 1 (ODr-S) was found to have no β-sheet of β1 and/or β2 as seen from FIG. 15.

Figure 16:
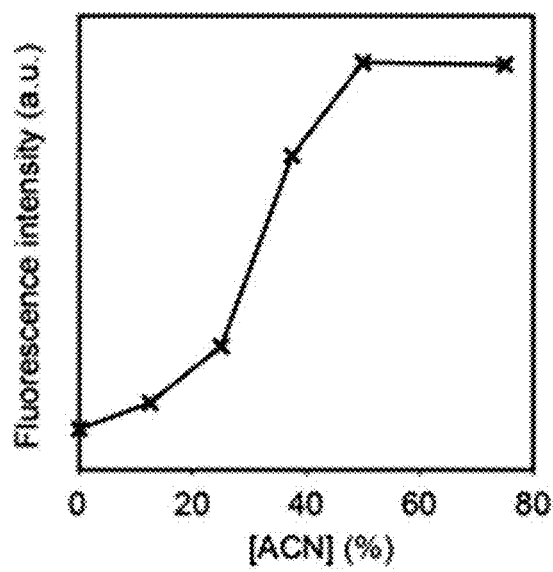
FIG. 16 shows a result of diluting a polypeptide prepared in Example 1 (ODβ-Lα) to a concentration of 0.5 μM and measuring the fluorescence intensity of the diluted polypeptide prepared in Example 1 (ODβ-Lα) at different ACN concentrations.

FIG. 16 shows a result of diluting the polypeptide prepared in Example 1 (ODβ-Lα) to a concentration of 0.5 μM and measuring the fluorescence intensity of the diluted polypeptide prepared in Example 1 (ODβ-Lα) at different ACN concentrations.

As seen from FIG. 16, the fluorescence intensity increased with the ACN concentration because the hydrophobic interaction of tryptophan and/or π-π interaction is decreased in the diluted polypeptide prepared in Example 1 (ODβ-Lα). Thus, it was confirmed that the diluted polypeptide prepared in Example 1 (ODβ-Lα) forms a pseudo-cyclic structure.

Figure 17:
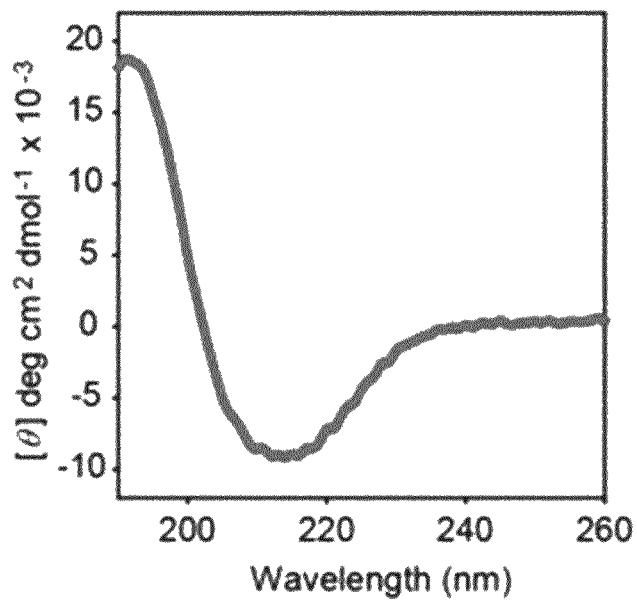
FIG. 17 shows a circular dichroism (CD) spectroscopy analysis result of a polypeptide prepared in Example 1 (ODβ-Lα).

FIG. 17 shows a circular dichroism (CD) spectroscopy analysis result of the polypeptide prepared in Example 1 (ODβ-Lα). It was found out that the polypeptide prepared in Example 1 (ODβ-Lα) consists of 17% of α-helices and 37% of β-sheets.

Figure 18:
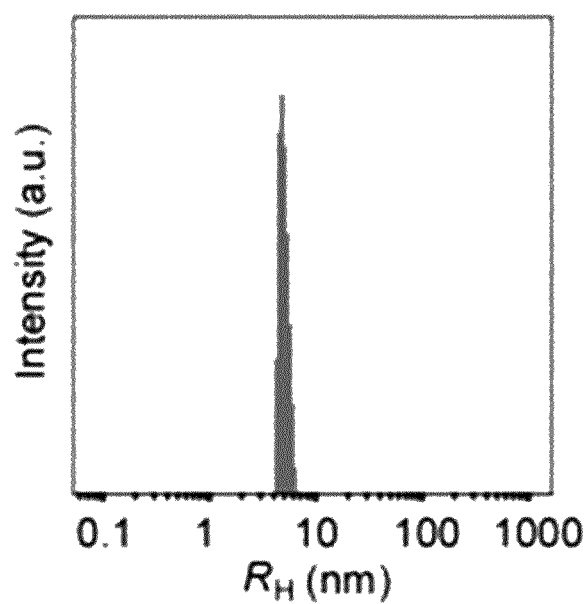
FIG. 18 shows dynamic light scattering (DLS) data of a polypeptide prepared in Example 1 (ODβ-Lα).

FIG. 18 shows dynamic light scattering (DLS) data of the polypeptide prepared in Example 1 (ODβ-Lα). $R_{(H)}$ was found to be ~5 nm.

Figure 19:
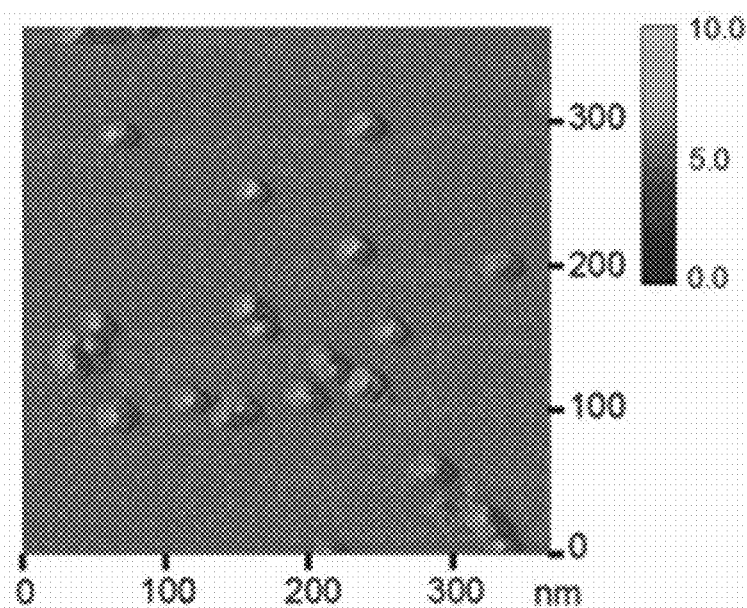
FIG. 19 shows an atomic force microscopic (AFM) image of a polypeptide prepared in Example 1 (ODβ-Lα).

FIG. 19 shows an atomic force microscopic (AFM) image of the polypeptide prepared in Example 1 (ODβ-Lα). The polypeptide prepared in Example 1 (ODβ-Lα) was found to have a length of ~15-18 nm. To compare this result with that of FIG. 13, the length was measured to be slightly longer due to tip broadening.

Figure 20:
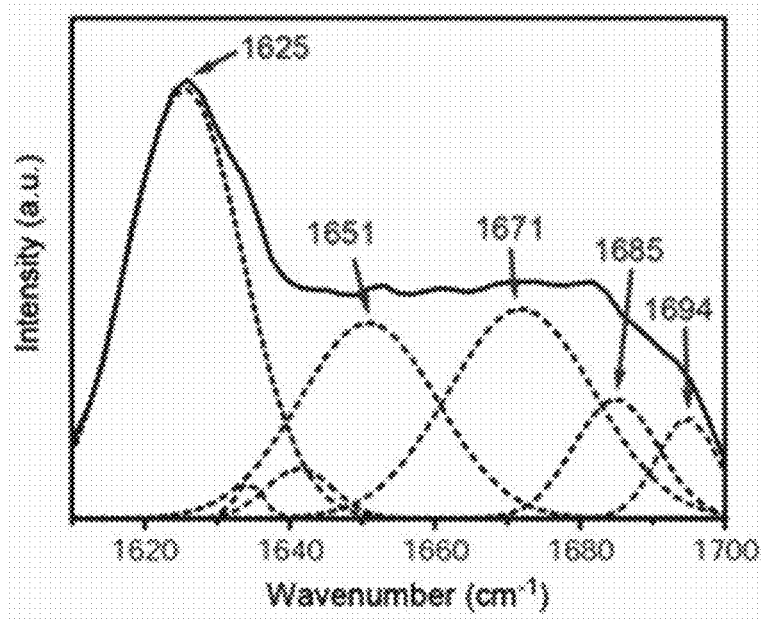
FIG. 20 shows infrared spectroscopy (IR) data of a polypeptide prepared in Example 1 (ODβ-Lα).

FIG. 20 shows infrared spectroscopy (IR) data of the polypeptide prepared in Example 1 (ODβ-Lα)

As seen from FIG. 20, an R1 β-sheet band was observed at 1625 cm$^{-1}$, an R2 α-helix band was observed at 1651 cm$^{-1}$ and R3 antiparallel β-sheets band were observed at 1685 and 1694 cm$^{-1}$. That is to say, it was confirmed that the polypeptide prepared in Example 1 (ODβ-Lα) has a βαβ motif structure consisting of the R1 and R3 β-sheets and the R2 α-helix wherein the R1 and R3 β-sheets have antiparallel structures.

Figure 21:
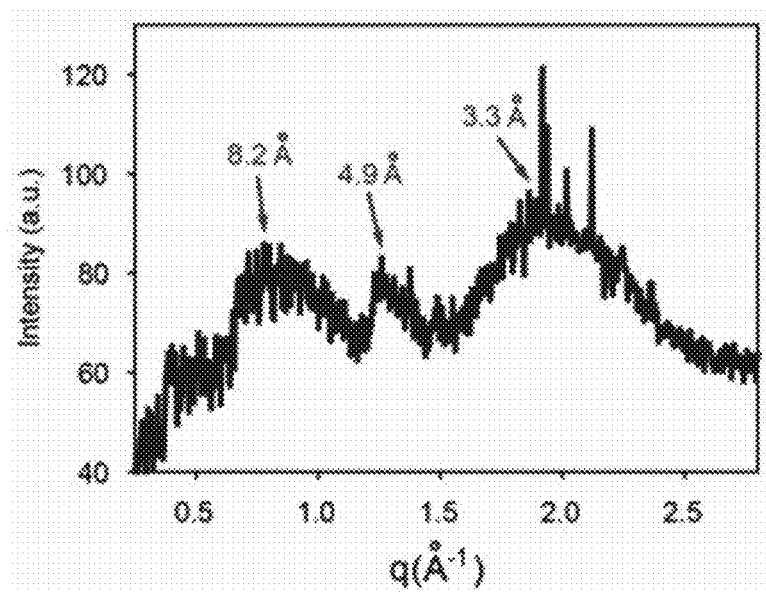
FIG. 21 shows wide-angle X-ray scattering (WAXS) data of a self-assembled nanostructure formed from the self-assembly of a polypeptide prepared in Example 1 (ODβ-Lα).

FIG. 21 shows wide-angle X-ray scattering (WAXS) data of a self-assembled nanostructure formed from the self-assembly of the polypeptide prepared in Example 1 (ODβ-Lα).

It was confirmed that the self-assembled nanostructure formed from the self-assembly of the polypeptide prepared in Example 1 (ODβ-Lα) had d-spacings of 3.3 Å, 4.9 Å and 8.2 Å. The 3.3 Å peak corresponds to the π-π interaction distance, the 4.9 Å peak corresponds to the (interstrand) distance between the β-sheets of β1 and β2 and the 8.2 Å peak corresponds to the intersheet distance. From this result, it was confirmed that the self-assembled nanostructure formed from the self-assembly of the polypeptide prepared in Example 1 (ODβ-Lα) has a bilayer structure:

In conclusion, it can be seen that the R1 and R3 β-sheets of the polypeptide prepared in Example 1 (ODβ-Lα) have antiparallel structures and a pseudo-cyclic structure is formed by hydrophobic and/or π-π interaction between them.

The α-helix structure of a in the polypeptide prepared in Example 1 (ODβ-Lα) is stabilized as it is constrained by the β-sheets of β1 and β2 and the pseudo-cyclic structure. In addition, it is further stabilized as the pseudo-cyclic structure is formed by the interaction between the β-sheets of β1 and β2.

In general, it is known that an α-helix is more constrained in a cyclic peptide. Although the polypeptide according to the present disclosure prepared in Example 1 (ODβ-Lα) has a linear structure, it forms a pseudo-cyclic structure similar to that of a cyclic peptide due to interaction between the β-sheets of β1 and β2 without introduction of a linker. As a result, the α-helix structure of α is further constrained and stabilized.

Since the polypeptide prepared in Example 1 (ODβ-Lα) has a basically linear structure and does not require an additional process such as cyclization during synthesis, it can be produced in large scale through a convenient and simple process.

Figure 22:
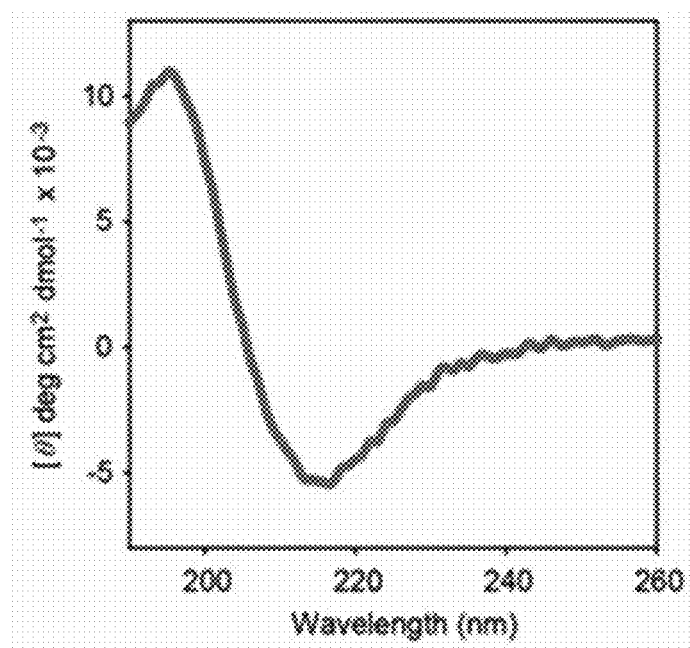
FIG. 22 shows a circular dichroism (CD) spectroscopy analysis of a polypeptide prepared in Comparative Example 2 (NDβ-Lα) in solution.

FIG. 22 shows a circular dichroism (CD) spectroscopy analysis of the polypeptide prepared in Comparative Example 2 (NDβ-Lα) in solution.

It can be seen that, when the polypeptide prepared in Comparative Example 2 (NDβ-Lα) remains dissolved in solution, parallel and antiparallel β-sheets of β1 and β2 exist together.

Figure 23:
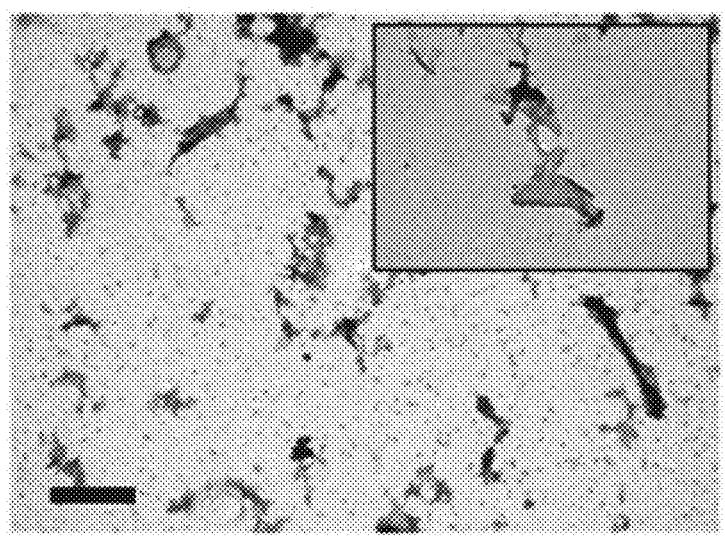
FIG. 23 shows a transmission electron microscopic (TEM) image of a negatively stained aggregate of a polypeptide prepared in Comparative Example 2 (NDβ-Lα). The insert is an enlarged image.

FIG. 23 shows a transmission electron microscopic (TEM) image of a negatively stained aggregate of the polypeptide prepared in Comparative Example 2 (NDβ-Lα). The insert is an enlarged image.

It can be seen that, in contrast to the polypeptide prepared in Example 1 (ODβ-Lα), the polypeptide prepared in Comparative Example 2 (NDβ-Lα) forms a heterogeneous structure and exists mainly as large-sized aggregates.

Based on this result, it is thought that the polypeptide prepared in Comparative Example 2 (NDβ-Lα) exists as random structures such as large aggregates because of random intramolecular interactions. That is to say, the polypeptide prepared in Comparative Example 2 (NDβ-Lα) fails to form a pseudo-cyclic structure as that of the polypeptide according to the present disclosure, because the β-sheets of β1 and β2 have parallel structures with weak hydrogen bonding and no linker exists that links the β-sheets of β1 and β2. As a result, an aggregate is formed as the β-sheets of β3 and/or β2 of adjacent polypeptides (NDβ-Lα) are arranged to have antiparallel structures.

What is claimed is:

1. A polypeptide, comprising R1, R2 and R3 domains, wherein a residue that links the R2 and the R3 is lysine (K) and the amino acid sequences of the R1 and the R3 have oppositional directionality and antiparallel structures when folded and self-assembled, and
wherein the polypeptide is represented by [Chemical Formula 1]:

[Chemical Formula 1]

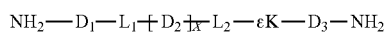

wherein each of $D_1$, $D_2$ and $D_3$ comprises 1-20 amino acids,
wherein each of $L_1$ and $L_2$ is a flexible linker comprising 1-8 amino acids,
wherein X is an integer from 2 to 10, and
wherein at least one of the following is true:
(i) R1 is [SEQ ID NO: 2];
(ii) R2 is [SEQ ID NO: 4];
(iii) R3 is [SEQ ID NO: 3];
(iv) $D_1$ is [SEQ ID NO: 2];
(v) $L_1$ is [SEQ ID NO: 7];
(vi) $D_2$ is [SEQ ID NO: 4];
(vii) x is 2;
(viii) $L_2$ is GS; and
(ix) D3 is [SEQ ID NO: 3].

2. A polypeptide, comprising R1, R2 and R3 domains, wherein a residue that links the R2 domain and the R3 domain is lysine (K) and the amino acid sequences of the R1 domain and the R3 domain have oppositional directionality and antiparallel structures when folded and self-assembled, and
wherein the polypeptide is represented by [Chemical Formula 1]:

[Chemical Formula 1]

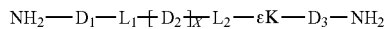

wherein each of $D_1$, $D_2$ and $D_3$ comprises 1-20 amino acids,
wherein each of $L_1$ and $L_2$ is a flexible linker comprising 1-8 amino acids, wherein the linkers are independently selected from the group consisting of glycine, glycine and serine, glycine and alanine, and alanine and serine, and
wherein X is an integer from 2 to 10.

3. The polypeptide according to claim 2, wherein the polypeptide has a folded structure wherein the R2 domain having an α-helix structure is located at a center and the R1 and R3 domains having β-sheet structures are linked at both ends of the R2 domain.

4. The polypeptide, comprising R1, R2 and R3 domains, wherein a residue that links the R2 and the R3 is lysine (K) and the amino acid sequences of the R1 and the R3 have oppositional directionality and antiparallel structures when folded and self-assembled, and
wherein the polypeptide is represented by [Chemical Formula 1]:

[Chemical Formula 1]

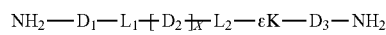

wherein each of $D_1$, $D_2$ and $D_3$ comprises 1-20 amino acids,
wherein each of $L_1$ and $L_2$ is a flexible linker comprising 1-8 amino acids,
wherein X is an integer from 2 to 10,
wherein the polypeptide comprises the sequence of [SEQ ID NOS 1 and 2]:
[SEQ ID NOS 1 and 2, respectively, in order of appearance]

(overhead dots for oppositely directed amino acid residues).

5. A self-assembled nanostructure formed as the polypeptide according to claim 2 is self-assembled.

6. The self-assembled nanostructure according to claim 5, wherein the self-assembled nanostructure has a bilayer structure.

7. The polypeptide according to claim 1, wherein R1 is [SEQ ID NO: 2].

8. The polypeptide according to claim 1, wherein R2 is [SEQ ID NO: 4].

9. The polypeptide according to claim 1, wherein R3 is [SEQ ID NO: 3].

10. The polypeptide according to claim 1, wherein $D_1$ is [SEQ ID NO: 2].

11. The polypeptide according to claim 1, wherein $L_1$ is [SEQ ID NO: 7].

12. The polypeptide according to claim 1, wherein $D_2$ is [SEQ ID NO: 4].

13. The polypeptide according to claim 1, wherein x is 2.

14. The polypeptide according to claim 1, wherein $L_2$ is GS.

15. The polypeptide according to claim 1, wherein $D_3$ is [SEQ ID NO: 3].

16. The polypeptide according to claim 1, wherein R1 is [SEQ ID NO: 2], R2 is [SEQ ID NO: 4], R3 is [SEQ ID NO: 3], $D_1$ is [SEQ ID NO: 2], $L_1$ is [SEQ ID NO: 7], $D_2$ is [SEQ ID NO: 4], x is 2, $L_2$ is GS, and $D_3$ is [SEQ ID NO: 3].

17. The polypeptide according to claim 1, wherein R1=WKWEWYWKWEW [SEQ ID NO: 2], R2=EAAAK [SEQ ID NO: 4], and R3=WEWKWYWEWKW [SEQ ID NO: 3].

18. The polypeptide according to claim 1, wherein $D_1$=WKWEWYWKWEW [SEQ ID NO: 2], $L_1$=GSGS, [SEQ ID NO: 7], $D_2$=EAAAK [SEQ ID NO: 4], x=2, $L_2$=GS, and $D_3$=WEWKWYWEWKW [SEQ ID NO: 3].

* * * * *